(12) United States Patent
Schilling

(10) Patent No.: US 7,376,298 B2
(45) Date of Patent: *May 20, 2008

(54) OPTICAL ROTATING DATA TRANSMISSION DEVICE WITH AN UNOBSTRUCTED DIAMETER

(75) Inventor: Harry Schilling, Eichstaett (DE)

(73) Assignee: Schleifring und Apparatebau GmbH, Fuerstenfeldbruck (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/278,069

(22) Filed: Mar. 30, 2006

(65) Prior Publication Data

US 2006/0177172 A1    Aug. 10, 2006

Related U.S. Application Data

(63) Continuation of application No. PCT/EP04/11283, filed on Oct. 8, 2004.

(30) Foreign Application Priority Data

Aug. 2, 2004    (DE) .................. 10 2004 037 684

(51) Int. Cl.
*G02B 6/26* (2006.01)
*H01J 40/14* (2006.01)

(52) U.S. Cl. ................ 385/25; 385/26; 385/31; 385/32; 385/37; 385/39; 250/216; 250/227.17

(58) Field of Classification Search .......... 385/25, 385/26, 1, 4, 31–32, 37, 39; 250/216, 227.12
See application file for complete search history.

(56) References Cited

U.S. PATENT DOCUMENTS 4,109,997 A    8/1978    Iverson
4,447,118 A    5/1984    Mulkey
4,525,025 A    6/1985    Hohmann et al.
4,555,631 A  * 11/1985    Martens ............... 250/551
4,647,767 A    3/1987    Jubinski
4,856,862 A    8/1989    Passmore et al.
4,934,783 A    6/1990    Jacobson (Continued)

FOREIGN PATENT DOCUMENTS

DE    19543386    3/1997

(Continued)

OTHER PUBLICATIONS

International Search Report, PCT/EP2004/011283, mailed Feb. 22, 2005.

*Primary Examiner*—Frank G. Font
*Assistant Examiner*—Michael P. Mooney
(74) *Attorney, Agent, or Firm*—Kevin L. Daffer; Daffer McDaniel, LLP

(57) ABSTRACT

A device for transmitting modulated optical signals between a first unit and a second unit, in which the first unit is supported to be rotatable relative to the second unit, comprises a light guide along a circular track on the first unit, a first light coupler for coupling light into or out of the light guide, and a second light coupler disposed on the second unit and movable relative to the light guide, for coupling light into or out of the light guide. A coupling of light into the light guide is effected by means of a beam splitters and a light deflecting means.

19 Claims, 2 Drawing Sheets

U.S. PATENT DOCUMENTS

| | | | | |
|---|---|---|---|---|
| 6,104,849 A | * | 8/2000 | Lewis et al. | 385/26 |
| 7,010,191 B2 | * | 3/2006 | Poisel et al. | 385/25 |
| 2005/0063709 A1 | * | 3/2005 | Poisel et al. | 398/152 |

FOREIGN PATENT DOCUMENTS

| | | |
|---|---|---|
| DE | 19625872 | 1/1998 |
| DE | 10029206 | 1/2002 |
| DE | 10256634 | 12/2003 |
| DE | 10230536 | 1/2004 |
| WO | WO 99/04309 | 8/2001 |
| WO | WO 03/069392 | 8/2003 |

* cited by examiner

OPTICAL ROTATING DATA TRANSMISSION DEVICE WITH AN UNOBSTRUCTED DIAMETER

CROSS REFERENCE TO RELATED APPLICATIONS

This application is a continuation of pending International Application No. PCT/EP2004/011283 filed Oct. 8, 2004, which designated the United States and claims priority from pending German Application No. 10 2004 037 684.0 filed Aug. 2, 2004.

BACKGROUND OF THE INVENTION

1. Field of the Invention

The invention relates to a device for transmitting optical signals between units that are rotatable relative to each other. Devices of this kind are used preferably in computer tomographs.

2. Description of the Prior Art

Various devices are known for transmitting optical signals between units that are rotatable relative to each other, particularly those having an unobstructed inner diameter. A basic problem existing here is that of designing a means for carrying light along the circumference of the device, and also suitable means for coupling light in and out. For use in computer tomographs, devices of this kind must have large unobstructed diameters of an order of magnitude of 1 meter. The circumferential speed of a rotation may be of an order of magnitude of 20 m/s. At the same time, data rates of more than 1 gigabit per second (Gbaud) must be feasible.

Thus, the U.S. Pat. No. 4,109,997 discloses an optical rotating data transmission device in which travel of light along the circumference occurs by reflection at two opposite faces. Light guides or glass fibers are provided for coupling light in or out, a bundling or focusing of the light beam being effected by means of lenses. Wideband data transmission with period lengths of a modulation signal which are substantially smaller than the transit time of the light around the circumference of the device is not possible, because a multiple-path reception of signals occurs at positions of a receiver close to a transmitter. Thus, signals received from the transmitter along a short path, and signals which have been reflected at least once around the circumference of the device, are received simultaneously. The transit time difference must be small in comparison with the period length of the modulation signal. Thus, with an inner diameter of about 1 meter, a total transit time around the circumference of about 10 nanoseconds results. For example, in a transmission of digital signals this makes it possible to achieve bit periods of maximally 50 nanoseconds, corresponding to a maximum transmission rate of 20 Mbaud.

An improvement of the optical system is disclosed in U.S. Pat. No. 4,525,025. This illustrates, particularly in FIG. 10, a specially suitable trench for transmitting optical signals with low attenuation. It consists only of one part, and can therefore be manufactured at favorable cost. However, this patent specification describes no effective solution of the problem of bandwidth limitation. In addition, the proposed coupling-in or coupling-out of light by blunt fiber ends can be achieved only with an extremely poor efficiency. Thus, this device is suitable only for small diameters. This device is extremely compact, but requires fiber couplers that maintain polarization when dividing the light from one single transmitter among a plurality of fibers for the purpose of feeding-in.

An improvement of optical coupling-in or coupling-out is disclosed in U.S. Pat. No. 4,555,631. In this, the coupling-in of optical signals into a mirror-finished cylinder is effected by means of two mirrors. For coupling-out, an additional coupling-out element is provided to be disposed at a fixed position in the trench. However, here too a large attenuation of the optical transmission path results, because the coupling-in mirrors cannot be placed arbitrarily close to the mirror-finished cylinder, in particular at high speeds of movement. Finally, the problem of bandwidth limitation is not solved. Thus, the light is conducted from a coupling-in position to a coupling-out position along two paths in opposite directions, and finally jointly evaluated in a receiver. Here too the limitation applies that the period length of the modulation signal must be substantially smaller than the transit time of the light around the circumference of the device. Finally, the contour of the mirror-finished trench must be adapted to the mirrors.

A device having an especially high optical efficiency is described in U.S. Pat. No. 4,934,783. In this, a focusing of the beam of rays is effected through a lens system. However, this system involves much outlay, is expensive to fabricate, and is suitable only for small diameters. Furthermore, here too the wideband problem has not been solved.

DE 195 43 386 C1 describes a device for wideband signal transmission with a possibility of a large bandwidth, but gives no indication of transmission with high transmission quality.

BRIEF SUMMARY OF THE INVENTION

The invention is based on the object of designing a relatively low-cost device for transmitting optical signals between two units that are rotatable relative to each other, and also a device for coupling-in optical signals into optical rotary joints in such manner that reliable transmission becomes possible with low optical attenuation for large diameters, high mechanical speeds of movement, and high data rates. It is another object of the invention to develop further a device of this kind so that signals are transmitted at a defined polarization. Furthermore, it is the object of a special development of the invention to design the device in such manner that even signals having period durations which are small in comparison with the time of propagation of the light around the circumference of the device may be transmitted.

In accordance with the invention, this object is achieved by a device for transmitting modulated optical signals between a first unit and a second unit, in which the first unit is supported to be rotatable relative to the second unit, comprising: a light source on the first unit for supplying optical energy; a light guide extending along a circular track on the first unit; at least one first light coupler connected to the light guide, for coupling light into or out of the light guide at a coupling-in or coupling-out position, respectively; and at least one second light coupler disposed on the second unit and movable relative to the light guide, for coupling light into or out of the light guide; wherein the at least one first light coupler comprises: an optical beam splitter for dividing optical energy supplied from the light source into similar light beams, of which a first light beam is coupled tangentially into the light guide to travel along a first light path extending along the light guide in a first direction, and a second light beam is coupled tangentially into the light guide to travel along a second light path extending along the light guide in a second direction opposite to the first direction; and at least one light deflecting means for deflecting the first light beam from the optical beam splitter to be tangentially directed into the light guide.

BRIEF DESCRIPTION OF THE DRAWINGS

In the following the invention will be described by way of example, without limitation of the inventive concept, on examples of embodiment with reference to the drawings.

DETAILED DESCRIPTION OF THE INVENTION

Figure 1:
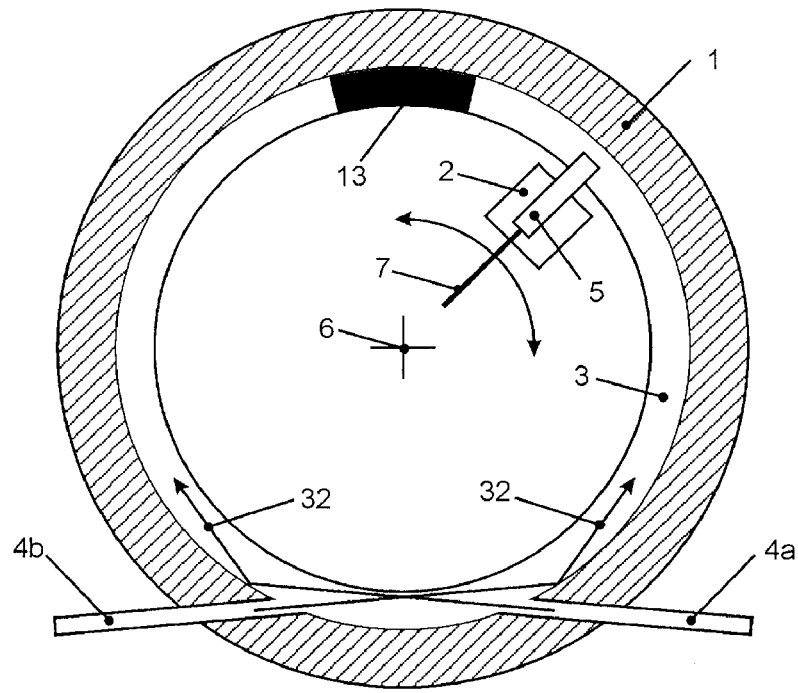
FIG. 1 schematically shows in a general form a device in accordance with the invention.

FIG. 1 shows in a schematic form a plan view of a part of a device according to the invention. A first unit (1) serves to accommodate an annular light guide (3). This light guide is, for example, a trench that is mirror-coated on the inside. A second unit (2) rotates relative to the first unit about a rotation axis (6). The second unit contains a second light coupler (5). The operation will now be illustrated separately for the two respective transmission directions from the first unit to the second unit, and from the second unit to the first unit. Transmission from the first unit to the second unit: light from a not illustrated transmitter is fed into the light guide (3) by means of both parts of a first light coupler (4a, 4b) at the same phase with respect to the modulation signal. On the right-hand side of the illustration the light from the first light coupler (4a) travels as far as the absorber (13). Simultaneously the light from the first light coupler (4b) travels as far as the absorber (13) on the left-hand side. The first light coupler (4) is here shown only schematically. A detailed illustration is given in the following Figures. The absorber is disposed symmetrically with respect to a coupling-in position of the first light coupler, so that the light paths (32) on both sides are of the same length. A tapping of the light is effected by means of a second light coupler (5) that is supported along the track of the light guide (3) to be rotatable around the rotation axis (6), and conducts the tapped light to an optical receiver. For the sake of simplicity, the optical receiver is also not illustrated. In the example shown, the mirror face of the beam splitter 73 is located on the hypotenuse of a half-cube.

Figure 2:
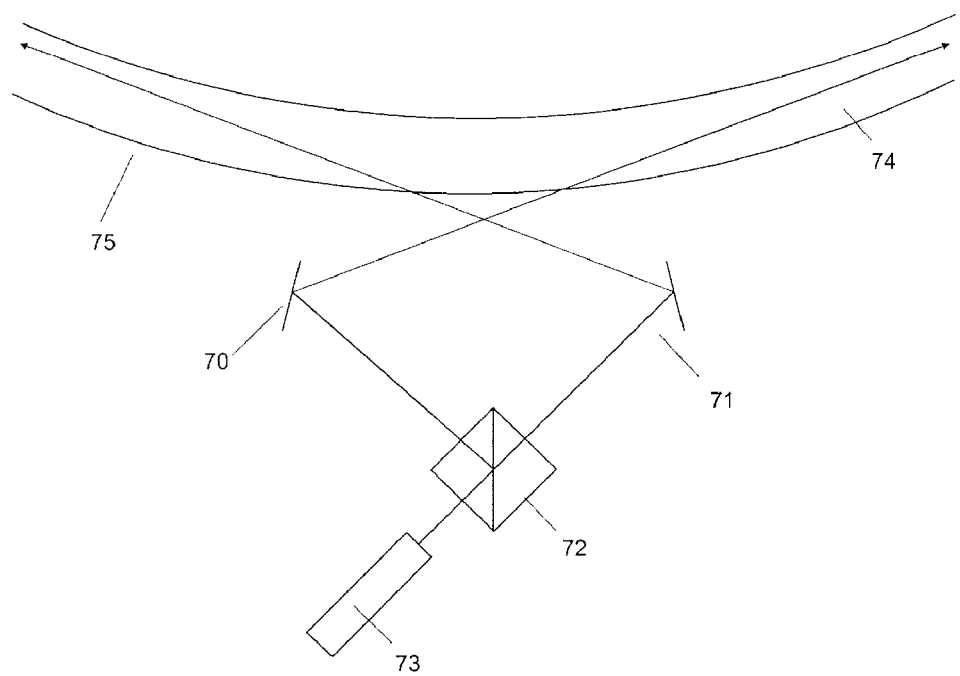
FIG. 2 schematically shows a first coupler in accordance with the invention.

FIG. 2 illustrates a first light coupler in accordance with the invention. The light emitted by a light source 73 is divided by a beam splitter 72 into two preferably similar beams. One of these beams is deflected by a first coupling mirror 70 into a first light path 74. The other beam is deflected via a second coupling mirror 71 into a second light path 75. The second light path 75 extends in a direction opposite to that of the first light path 74. Thus, light is now coupled into the light guide 3 in two opposite directions. The light travels in the light guide 3 as far as the absorber 13. For wideband signal transmission it is essential that the two light paths within the light guide 3 have no phase shift relative to each other. For this, the phase of the two light beams must be the same at the location of the first coupler, or the crossing point of the light beams in the region of the first coupler, and also at the position of the absorber. This can only be achieved when the two light paths within the light guide have the same length, and the optical path lengths from the light source 13 to the coupling-in position into the light guide are of equal length for the two light paths. Instead of a division of the light of the light guides 71 into two beams, it could be divided also into a larger number of light beams. In such a case, all of these light beams have the same optical energy.

Figure 3:
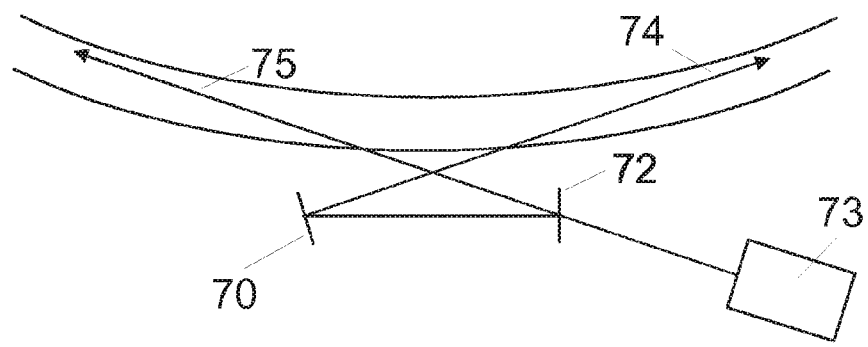
FIG. 3 illustrates another coupler embodiment of the present invention.

FIG. 3 shows another embodiment of the invention. The light emitted by the light source 73 is divided by the beam splitter 72 into preferably two similar beams. One of these beams is deflected into the first light path 74 by the first coupling mirror 70. The other beam is sent directly into the second light path 75.

Figure 4:
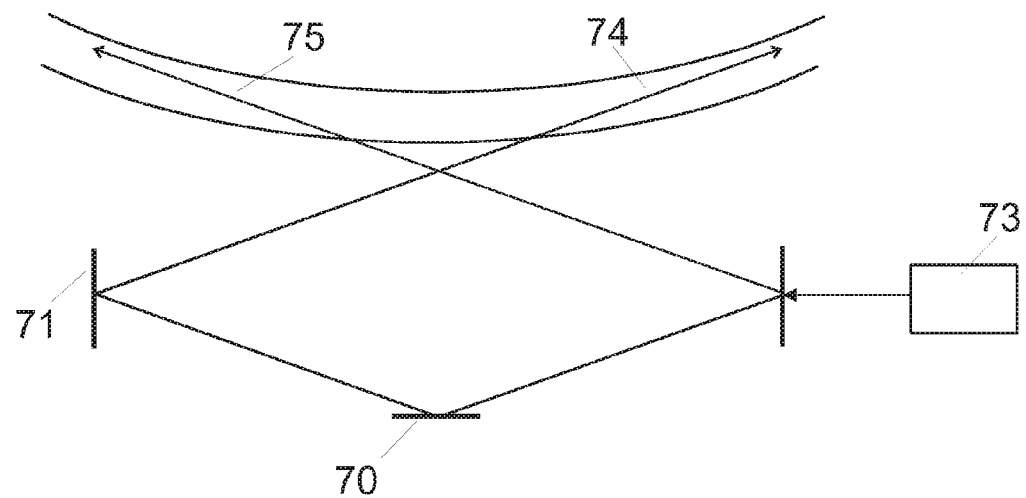
FIG. 4 schematically shows the transmission of optical signals from a first unit to a second unit.

Another embodiment of the invention is illustrated in FIG. 4. In this, the first beam from the beam splitter 72 is deflected into the first light path 74 by means of a first coupling mirror 70 and a second coupling mirror 71.

The device in accordance with the invention comprises a light guide that is disposed along a circular track on a first unit. For the sake of simplicity only one light guide will be described here. Of course, a plurality of arrangements in accordance with the invention, each having one light guide, may be connected in parallel. Connected to the light guide is at least one first light coupler for coupling light into or out of the light guide. At least one optical transmitter or receiver is connected to at least one of these light couplers. Whether a transmitter or receiver is to be connected to the light guide is determined by the desired direction of transmission. If light is to be transmitted away from the light guide, then a transmitter must be provided, and a receiver in the other case. Of course, for transmitting information, the optical transmitters are adapted to be modulated with a modulation signal.

Furthermore, a second unit is provided that is supported to be rotatable with respect to the first unit. A basic concept applied here is that of relative movement of the two units with respect to each other, and no reference will be made to rotating or stationary units, because this is exclusively a question of reference to location. To this second unit is assigned at least one second light coupler that moves, together with a rotation of the second unit relative to the first, along a predetermined track relative to the light guide. At least one of these second light couplers is equipped in a manner complementary to that of the first light guide, optionally with an optical transmitter or receiver.

Now, in order to achieve as large as possible a bandwidth, it is necessary to couple light through a first light coupler 4 into the light guide 3 along two circular light paths extending in opposite directions. In an arrangement of this kind, an absorber 13 is inserted into the light guide preferably opposite to the middle of the first light guide, so that two equally long branches of the light guide result. Because no phase shifts must occur when the second light coupler passes the absorber or the mid-point of the first light guide, the signals circulating in opposite directions along the two equally long branches of the light guide must be fed in through the first light coupler with the same phase, so that they may be absorbed in the absorber also with the same phase from both sides. This same phase position is achieved by equal optical path lengths of both optical paths in the first light coupler. In a first light coupler in accordance with the invention, the light from a light source 73 is split by means of an optical beam splitter 72 into preferably two similar light beams. These are now fed tangentially into the light guide 3, in particular by means of a first coupling mirror 70 into a first light path 74, and by means of a second coupling mirror 71 into a second light path 75 extending circularly in a direction opposite to that of the first light path. For this, the first light guide is disposed to be outside the radius of the light guide. By using the beam splitter that receives the polarization of the light from the light source 73, and the coupling mirrors 70 and 71, light having the same polarization can be coupled into the two branches of the light guide. Of course, the principle illustrated here on an example of two light beams can be applied also to 3, 4, or more light beams.

Another embodiment of the invention provides for light from a light source 73 to be divided by an optical beam splitter 72 into two preferably similar light beams. The first of these light beams is coupled tangentially into the light guide 3 by means of a first coupling mirror 70. The second light beam is coupled directly, i.e. without a coupling mirror, tangentially into the light guide to travel circularly in an opposite direction to the first light beam. In order to achieve here as small as possible a phase shift between the first and the second light beam, the arrangement should be configured to be as small as possible.

Another embodiment of the invention provides a hydrostatic or hydrodynamic bearing means. For this, at least one second light coupler 5 is positioned opposite to the light guide along one or two axes with the hydrostatic or hydrodynamic bearing means.

A hydrostatic or hydrodynamic bearing means of this kind is based on a thin gas film or liquid film, preferably an air film between two plane surfaces. The film is of high stiffness, so that large changes of force lead to only minor changes of spacing.

In the case of a gas film, preferably an inert gas such as, for example, nitrogen or preferably a noble gas is used. The film-forming material or the gas is preferably transparent or non-absorbing at the wavelength used for optical transmission. With this, a penetration of the medium into the light guide causes no interference with transmission. Similarly, the medium may be directed into the light guide on purpose, for example to keep it free from external contamination, or to clean it.

Further suitable media are also liquids that pass over into a gaseous state at the operating temperature of the device. This makes possible a simultaneous cooling of the system, particularly under difficult conditions.

In the case of a hydrostatic bearing means, the supply of the medium to the bearing is effected preferably by means of a small pump or a pressure vessel. Here the medium is urged in between the two plane bearing faces. As such bearings use only smallest gas or air quantities because of the small spacing and the high surface quality of the bearing faces, a supply of this kind can be effected with low-cost means.

As an alternative to this, in the case of a hydrodynamic bearing means the supply can be effected using the air stream caused by the movement of the two units relative to each other. In this case, the bearing action is effected by the streaming (hydrodynamic paradoxon, Bernoulli effect). For this, preferably means are provided for conducting an air current caused by the movement in between the bearing faces. In the simplest case, air guiding elements consist of a simple air guide sheet for suitably redirecting a part of the air currents. Similarly, more complex embodiments can be conceived, which for example contain additional filters in order to free the air steam from particles that are large, or small but troublesome. Optionally, arrangements can also be used which, for example, provide for an air velocity that is substantially independent of the speed of the movement. Thus, an independence of the air streaming velocity with increasing speed of movement can be achieved by means of an element which provides for an increasing turbulence of air. A bearing means of this kind must, of course, have emergency running properties for the case of low speeds. These may be achieved, for example by additional combination with a hydrostatic design.

Especially favorable is a combination of a hydrodynamic or hydrostatic bearing means together with an active position regulation. They may be used, for example, along the same axis for particularly precise alignment, or also in supplementary manner along different axes. Thus, for example, the position regulation may be effected by control of air stream or air pressure of a hydrodynamic or hydrostatic bearing means. This combination yields, on the one hand, a mechanically robust system, and this is provided with highly precise characteristics by an additional, superposed regulation. With this, in particular, even tolerances of the spacing of an air bearing means, caused by temperature and humidity fluctuations of the air, and also fluctuations of the velocity, may be counterbalanced.

Another advantageous embodiment of the invention provides for at least one beam splitter 73 have structured mirror coatings. Coatings of this kind are applied on the surface of a substrate preferably by injection molding methods or by sputtering. The structure could be configured, for example, as a grid, a hexagonal pattern or a random pattern. Preferably, this pattern covers one half of the cross-section of the beam from the light source 73. With this, the beam is partially or half reflected by the structured mirror coating along the direction of the first light path. The remainder of the light is relayed directly along the direction of the second light path 75, or by means of a second coupling mirror 71. The splitting ratio of this beam splitter can be precisely set by adjusting the relative coverage of the surface of the transparent substrate by the mirror coating. This type of beam splitter is sometimes also referred to as a "polka-dot" beam splitter.

Another embodiment of the invention comprises a very thin metal layer on a transparent substrate. A first part of the light from the light source 73 can pass through the thin metal layer in the direction of the first coupling mirror 70, whilst another part of the light is deflected in the direction of the second coupling mirror 71. The splitting ratio of this beam splitter preferably may be set by adjusting the thickness of the metal layer.

In another embodiment of the invention, the beam splitter 72 comprises at least one multiple-layer system of various layers of metallic and dielectric materials, in order to achieve a constant splitting ratio for all possible conditions of polarization. Multiple-layer systems of this kind are usually dependent upon the optical wavelength, and in most cases can be used only in a narrow band. By a use of multiple-layer systems of this kind, changes of the polarization can be minimized. Preferably the layers are disposed on a plane-parallel plate or the hypotenuse of a half-cube. Light from the light source is normally incident at an angle of 45° on the surface of this system. The embodiment with a half-cube has the advantage that there is no parallel shift of the transmitted light beam.

Another embodiment of the invention comprises a holographic optical element (HOE) as a beam splitter. The holographic layer is able to deflect incident light in different directions. Thus, the light can be divided into the two light paths 74 and 75. Alternatively, the holographic optical elements can also be designed to deflect the light along different light paths, preferably in dependence upon the wavelength.

In another embodiment of the invention, at least one optical grating is provided in the optical beam splitter 72.

Preferably at least one optical grating is designed to be reversible. In this embodiment, the deflection of the light is caused by the grating which is wavelength-selective. Preferably the grating con be controlled by a supply of energy. A grating of this kind could be based, for example, on liquid crystals, the orientation of which is controlled by electric fields.

Another embodiment of the invention comprises an optical switch. A switch of this kind may be designed so that it controls light from the light source in only one branch of the light guide. This means that light is coupled exclusively into the part of the light guide in which at least one second light coupler 5 for coupling-out is located. An optical switch of this kind could comprise liquid crystals, for example. The advantage of an optical switch in accordance with the invention is that the light from the light source 73 need not be divided along two paths, but that the entire optical energy can be fed into that branch of the light guide 3 in which a light coupler 5 happens to be located.

The invention claimed is:

1. Device for transmitting modulated optical signals between a first unit and a second unit, in which the first unit is supported to be rotatable relative to the second unit, comprising:
   a light source on the first unit for supplying optical energy;
   a light guide extending along a circular track on the first unit;
   at least one first light coupler connected to the light guide, for coupling light into or out of the light guide at a coupling-in or coupling-out position, respectively;
   at least one second light coupler disposed on the second unit and movable relative to the light guide, for coupling light into or out of the light guide; and
   wherein the at least one first light coupler comprises:
      an optical beam splitter for dividing optical energy supplied from the light source into similar light beams, of which a first light beam is coupled tangentially into the light guide to travel along a first light path extending along the light guide in a first direction, and a second light beam is coupled tangentially into the light guide to travel along a second light path extending along the light guide in a second direction opposite to the first direction, and wherein the beam splitter further comprises at least one optical switch provided for switching light from the light source into a selected light path in which at least one second light coupler is located; and
      at least one light deflecting means for deflecting the first light beam from the optical beam splitter to be tangentially directed into the light guide.

2. Device according to claim 1, wherein the at least one first light coupler is disposed outside a radius of the light guide.

3. Device according to claim 1, wherein the optical beam splitter divides the optical energy supplied from the light source into two similar beams.

4. Device according to claim 1, wherein the deflecting means comprises a first coupling mirror for deflecting the first light beam from the optical beam splitter to be tangentially directed into the light guide, and a second coupling mirror for deflecting the second light beam from the optical beam splitter to be tangentially directed into the light guide.

5. Device according to claim 1, wherein the deflecting means comprises a first coupling mirror for deflecting the first light beam from the optical beam splitter to be tangentially directed into the light guide, and the second light beam from the optical beam splitter is directly coupled into the second light path.

6. Device according to claim 1, wherein the deflecting means comprises a first and a second coupling mirror for deflecting the first light beam from the optical beam splitter to be tangentially directed into the light guide.

7. Device according to claim 1, wherein hydrostatic or hydrodynamic bearing means are provided to hold at least one second light coupler in a defined position with respect to the light guide along at least one axis perpendicular to the tangent to the rotary motion of the two units with the aid of a liquid or gaseous medium, or a bearing means based on a liquid or a gaseous medium.

8. Device according to claim 7, wherein the hydrostatic or hydrodynamic bearing means hold the at least one second light coupler in a defined position with respect to the light guide along two axes perpendicular to the tangent to the rotary motion of the two units with the aid of a liquid or gaseous medium, or a bearing means based on a liquid or a gaseous medium.

9. Device according to claim 7, wherein the gaseous medium is air.

10. Device according to claim 1, wherein the beam splitter comprises structured mirror coatings on a transparent substrate.

11. Device according to claim 10, wherein the structured mirror coatings have been applied onto the transparent substrate with a melting process or by sputtering.

12. Device according to claim 10, wherein the structured mirror coatings have a structure similar to that of one selected from a grid, a hexagonal pattern, and a random pattern.

13. Device according to claim 1, wherein the beam splitter comprises a very thin metal film that has been applied onto a transparent substrate.

14. Device according to claim 13, wherein the very thin metal film has been applied onto a transparent substrate with a melt process or by sputtering.

15. Device according to claim 1, wherein the beam splitter comprises at least one multi-layer system with a plurality of layers of metallic and dielectric materials.

16. Device according to claim 15, wherein the layers are disposed on a plane-parallel plate or the hypotenuse of a half-cube.

17. Device according to claim 1, wherein the beam splitter comprises at least one holographic optical element.

18. Device according to claim 1, wherein the beam splitter comprises at least one optical grating.

19. Device according to claim 18, wherein the at least one optical grating is reversible.

* * * * *